(12) United States Patent
Ainger et al.

(10) Patent No.: US 7,781,386 B2
(45) Date of Patent: Aug. 24, 2010

(54) SHAMPOO COMPOSITIONS CONTAINING A COMBINATION OF CATIONIC POLYMERS

(75) Inventors: Nicholas John Ainger, Wirral (GB); Jayne Lesley Dawson, Wirral (GB); Emmanuel Paul Jos Marie Everaert, Wirral (GB); Neil Scott Shaw, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/086,093

(22) PCT Filed: Nov. 15, 2006

(86) PCT No.: PCT/EP2006/010954

§ 371 (c)(1), (2), (4) Date: Jan. 8, 2009

(87) PCT Pub. No.: WO2007/066537

PCT Pub. Date: Jun. 14, 2007

(65) Prior Publication Data

US 2009/0197784 A1 Aug. 6, 2009

(30) Foreign Application Priority Data

Dec. 8, 2005 (EP) .................................. 05257543
Mar. 8, 2006 (GB) .................................. 0604656.9

(51) Int. Cl.
*C11D 3/37* (2006.01)
*C11D 9/36* (2006.01)

(52) U.S. Cl. .................. 510/122; 510/119; 510/121; 510/127; 510/130; 510/466; 510/473; 510/504

(58) Field of Classification Search .................. 510/119, 510/121, 122, 130, 466, 473, 504
See application file for complete search history.

(56) References Cited

U.S. PATENT DOCUMENTS

2003/0109391 A1* 6/2003 Midha et al. ................. 510/122
2004/0157754 A1* 8/2004 Geary et al. ................. 510/119
2005/0100522 A1* 5/2005 Chappell et al. ........... 424/70.12
2005/0143268 A1* 6/2005 Midha et al. ................. 510/130
2005/0180941 A1* 8/2005 Doi et al. .................. 424/70.27
2006/0079422 A1* 4/2006 Midha et al. ................. 510/130
2006/0089342 A1* 4/2006 Gavin et al. ................... 514/184
2007/0009463 A1* 1/2007 Niebauer et al. ........... 424/70.7
2007/0110700 A1* 5/2007 Wells et al. .............. 424/70.21
2008/0138442 A1* 6/2008 Johnson et al. .............. 424/642

FOREIGN PATENT DOCUMENTS

| EP | 0 529 883 | 3/1993 |
| EP | 1 329 214 | 7/2003 |
| EP | 1 366 742 | 12/2003 |
| WO | 00/66080 | 11/2000 |
| WO | 03/005986 | 1/2003 |
| WO | 2004/043414 | 5/2004 |

OTHER PUBLICATIONS

PCT International Search Report in PCT application PCT/EP2006/010954.

* cited by examiner

*Primary Examiner*—Charles I Boyer
(74) *Attorney, Agent, or Firm*—Ronald A. Koatz

(57) ABSTRACT

The invention provides an aqueous shampoo composition comprising: (i) one or more anionic cleansing surfactants; (ii) preferably, discrete, dispersed droplets of a water-insoluble conditioning agent with a mean droplet diameter ($D_{3,2}$) of 4 micrometers or less; (iii) one or more cationic polymers (A) selected from cationically modified acrylamide polymers having a cationic charge density at pH7 of less than 1.0 meq per gram, cationically modified celluloses and mixtures thereof, and (iv) one or more cationic polymers (B) selected from cationically modified acrylamide polymers having a cationic charge density at pH7 of greater than 1.0 meq per gram, cationically modified polygalactomannans, and mixtures thereof, wherein the composition comprises a cationic polymer other than a cationically modified acrylamide polymer.

5 Claims, No Drawings

SHAMPOO COMPOSITIONS CONTAINING A COMBINATION OF CATIONIC POLYMERS

FIELD OF THE INVENTION

This invention relates to shampoo compositions containing a combination of cationic polymers.

BACKGROUND AND PRIOR ART

Shampoo compositions comprising various combinations of cleansing surfactant and conditioning agents are known. These products typically comprise an anionic cleansing surfactant in combination with a conditioning agent. Amongst the most popular conditioning agents used in shampoo compositions are oily materials such as mineral oils, naturally occurring oils such as triglycerides and silicone polymers. These are generally present in the shampoo as dispersed hydrophobic emulsion droplets. Conditioning is achieved by the oily material being deposited onto the hair resulting in the formation of a film.

However, many shampoo compositions do not provide a sufficient level of deposition of conditioning agent onto the hair and skin during the cleansing process. Without such deposition, large proportions of conditioning agent are rinsed away during the cleansing process and therefore provide little or no conditioning benefit.

One known method for improving deposition of a conditioning agent from such shampoo compositions involves the use of cationic deposition polymers. These polymers may be synthetic or natural polymers that have been modified with cationic substituents.

A problem associated with the use of cationic deposition polymers is that is difficult to obtain a good balance of conditioning benefits at different stages of the shampooing process.

For example, some cationic deposition polymers are effective at improving wet stage hair sensory attributes during the stages of washing and rinsing, but give an undesirable hair feel after drying.

The present inventors have found that this problem can be overcome by using a specific combination of cationic polymers in a shampoo composition which comprises small droplets of a water-insoluble oily conditioning agent.

In particular, shampoo compositions of the invention give improved wet conditioning benefits, such as soft feel, smooth feel and combability when wet, with a reduction in dry hair sensory negatives such as the heavy, greasy or coated feel that many consumers experience when high charge density cationic polymers and oily conditioning agents are combined in shampoos.

SUMMARY OF THE INVENTION

The present invention provides an aqueous shampoo composition comprising:
(i) one or more anionic cleansing surfactants;
(ii) discrete, dispersed droplets of a water-insoluble conditioning agent with a mean droplet diameter ($D_{3,2}$) of 4 micrometres or less;
(iii) one or more cationic polymers (A) selected from cationically modified acrylamide polymers having a cationic charge density at pH7 of less than 1.0 meq per gram, cationically modified celluloses and mixtures thereof, and
(iv) one or more cationic polymers (B) selected from cationically modified acrylamide polymers having a cationic charge density at pH7 of greater than 1.0 meq per gram, cationically modified polygalactomannans, and mixtures thereof, wherein the composition comprises a cationic polymer other than a cationically modified acrylamide polymer.

DETAILED DESCRIPTION OF THE INVENTION

By "aqueous shampoo composition" is meant a composition which has water or an aqueous solution or a lyotropic liquid crystalline phase as its major component. Suitably, the composition will comprise from 50% to 98% by weight based on total weight of water, preferably from 60% to 90%.

Anionic Cleansing Surfactant

Shampoo compositions according to the invention comprise one or more anionic cleansing surfactants, which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate(n)EO, (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid (n) EO (where n is from 10 to 20).

Mixtures of any of the foregoing anionic cleansing surfactants may also be suitable.

The total amount of anionic cleansing surfactant in shampoo compositions of the invention generally ranges from 0.5 to 45%, preferably from 1.5 to 35%, more preferably from 5 to 20% by total weight anionic cleansing surfactant based on the total weight of the composition.

Water-insoluble Conditioning Agent

Shampoo compositions according to the invention comprise discrete, dispersed droplets of a water-insoluble conditioning agent with a mean droplet diameter ($D_{3,2}$) of 4 micrometres or less.

By "water-insoluble", it is meant that the material so described has a solubility in water at 25° C. of 0.1% by weight or less.

Preferably the mean droplet diameter ($D_{3,2}$) is 1 micrometre or less, more preferably 0.5 micrometre or less, and most preferably 0.2 micrometre or less.

A suitable method for measuring the mean droplet diameter ($D_{3,2}$) is by laser light scattering using an instrument such as a Malvern Mastersizer.

Preferably the conditioning agent is non-volatile, meaning that it has a vapour pressure of less than 1000 Pa at 250° C.

Preferred water-insoluble conditioning agents are emulsified silicones.

Suitable emulsified silicones include those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone.

Silicones that may be used as emulsified silicones in the present invention preferably have a molecular weight of greater than 100,000 and more preferably a molecular weight of greater than 250,000.

Silicones that may be used as emulsified silicones in the present invention preferably have a kinematic viscosity of greater than 50,000 cS ($mm^2.s^{-1}$) and more preferably a kinematic viscosity of greater than 500,000 cS ($mm^2.s^{-1}$). Kinematic viscosities as referred to in this specification are measured at 25° C. and can be measured by means of a glass capillary viscometer as set out further in Dow Corning Corporate Test Method CTM004 Jul. 20, 1970.

Suitable emulsified silicones for use in compositions of the invention are available as pre-formed silicone emulsions from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC2-1785, DC-1786, DC-1788 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

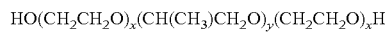

wherein the mean value of x is 4 or more and the mean value of y is 25 or more.

Another preferred form of the surface active block copolymer is according to the following formula:

wherein the mean value of a is 2 or more and the mean value of b is 6 or more.

Mixtures of any of the above described silicone emulsions may also be used.

Other suitable water-insoluble conditioning agents include non-silicone oily or fatty materials such as hydrocarbon oils, fatty esters and mixtures thereof.

Suitable hydrocarbon oils are characterised by having at least 12 carbon atoms, and include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Also suitable are polymeric hydrocarbons of $C_{2-6}$ alkenyl monomers, such as polyisobutylene.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used. Preferred fatty esters are mono-, di- and triglycerides, more specifically the mono-, di-, and tri-esters of glycerol with long chain carboxylic acids such as $C_{1-22}$ carboxylic acids. Examples of such materials include cocoa butter, palm stearin, sunflower oil, soyabean oil and coconut oil.

Mixtures of any of the above described conditioning agents may also be used.

The total amount of water-insoluble conditioning agent in compositions of the invention may suitably range from 0.05 to 10 preferably from 0.2 to 5%, more preferably from 0.5 to 3% by total weight water-insoluble conditioning agent based on the total weight of the composition.

Cationic Polymer

Cationically modified acrylamide polymers should be understood to be cationic polymers formed from a substantial quantity of acrylamide monomers, acrylamide monomers typically comprising at least 25 mole % and more typically at least 50 mole % of the monomers of the polymer. Acrylamide monomers should be understood include methacrylamide and N-alkyl acrylamides and methacrylamides, including functionalised versions thereof.

Suitable cationically modified acrylamide polymers for use as cationic polymers falling within group (A) or (B) include those formed from acrylamide monomers having cationic amine or quaternary ammonium functionalities, optionally together with non-cationic spacer monomers.

Suitable acrylamide monomers having cationic amine or quaternary ammonium functionalities include dialkylaminoalkyl acrylamide and dialkylaminoalkyl methacrylamide. The alkyl portions of these monomers are preferably lower alkyls such as the $C_1$, $C_2$ or $C_3$ alkyls.

Suitable non-cationic spacer monomers include (meth) acrylamide, alkyl and dialkyl (meth) acrylamides, alkyl (meth)acrylate, vinyl caprolactone and vinyl pyrrolidine. The alkyl and dialkyl substituted monomers preferably have $C_{1-7}$ alkyl groups, more preferably $C_{1-3}$ alkyl groups. Other suitable water-soluble spacer monomers include vinyl esters, vinyl alcohol, maleic anhydride, propylene glycol and ethylene glycol.

The ratio of the cationic to non-cationic monomers is selected to give polymers having a cationic charge density in the required range.

The cationic charge density of the polymer may suitably be determined via the Kjeldahl method as described in the US Pharmacopoeia under chemical tests for nitrogen determination and is expressed in milli-equivalents (meq) per gram.

Shampoo compositions according to the invention comprise one or more cationic polymers (A) selected from cationically modified acrylamide polymers having a cationic charge density at pH7 of less than 1.0 meq per gram, cationically modified celluloses and mixtures thereof.

Cationically modified celluloses are a preferred class of cationic polymer for use as cationic polymers (A) in the invention.

Suitable cationically modified celluloses have a hydrophilic cellulose backbone modified with cationic substituent groups.

The hydrophilic cellulose backbone can suitably be a hydrophilic cellulose such as hydroxymethylcellulose, hydroxyethylcellulose, hydroxyethyl ethylcellulose, hydroxypropylcellulose, hydroxypropyl methylcellulose, hydroxybutylcellulose and mixtures thereof.

Hydroxyethylcellulose is preferred.

Suitable cationic substituent groups have the general formula:

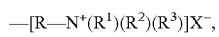

—[R—N$^+$(R$^1$)(R$^2$)(R$^3$)]X$^-$, in which R is an alkylene, oxyalkylene, polyoxyalkylene, or hydroxyalkylene group, or combination thereof, R$^1$, R$^2$ and R$^3$ independently represent alkyl, aryl, alkylaryl, arylalkyl, alkoxyalkyl, or alkoxyaryl groups, each group containing up to about 24 carbon atoms, and X is a counterion.

Preferably R is a hydroxyalkylene group of formula —CH$_2$CH(OH)CH$_2$—.

Preferably R$^1$ and R$^2$ are alkyl groups having from 1 to 7 carbon atoms, more preferably from 1 to 3 carbon atoms. Most preferably, R$^1$ and R$^2$ are both methyl.

Preferably R$^3$ is an alkyl group having from 1 to 7 carbon atoms, more preferably from 1 to 3 carbon atoms, most preferably methyl, or an alkyl group having from 8 to 22 carbon atoms, more preferably from 10 to 18 carbon atoms, most preferably dodecyl, or a mixture thereof.

Suitable cationically modified celluloses have a weight average molecular weight (M$_w$) of from 10,000 to 10,000,000, preferably from 50,000 to 5,000,000, most preferably from 100,000 to 3,000,000 Daltons.

Preferred cationically modified celluloses have a cationic charge density at pH7 ranging from 0.2 to 2 meq per gram.

Specific examples of preferred cationically modified celluloses for use as cationic polymers (A) in the invention are quaternized hydroxyethyl cellulose polymers with cationic substitution of trimethylammonium, having the INCI name Polyquaternium-10. Suitable materials of this type are commercially available from Amerchol Corporation in their UCARE™ Polymer JR, LK and LR series of polymers, such as UCARE™ Polymer JR30M, UCARE™ Polymer LR30M, UCARE™ Polymer JR400, UCARE™ Polymer LR400 and UCARE™ Polymer LK.

Also preferred for use as cationic polymers (A) in the invention are quaternized hydroxyethyl cellulose polymers with cationic substitution of trimethylammonium and dimethyldodecyl ammonium, having the INCI name Polyquaternium-67. Suitable materials of this type are commercially available from Amerchol Corporation in their SoftCAT™ SL and SK series of polymers, such as SoftCAT™ SL 5 Conditioning Polymer, SoftCAT™ SL 30 Conditioning Polymer, SoftCAT™ SL 60 Conditioning Polymer, SoftCAT™ SL 100 Conditioning Polymer, SoftCAT™ SK-L Conditioning Polymer, SoftCAT™ SK-M Conditioning Polymer, SoftCAT™ SK-MH Conditioning Polymer and SoftCAT™ SK-H Conditioning Polymer.

Mixtures of any of the above-described materials may also be suitable.

The total amount of cationic polymer (A) in compositions of the invention may suitably range from 0.001 to 1.0%, preferably from 0.01 to 0.5%, most preferably from 0.1 to 0.3% by total weight cationic polymer (A) based on the total weight of the composition.

Shampoo-compositions according to the invention comprise one or more cationic polymers (B) selected from cationically modified acrylamide polymers having a mean cationic charge density at pH7 of greater than 1.0 meq per gram, cationically modified polygalactomannans, and mixtures thereof.

Preferred cationically modified acrylamide polymers are those in which the vinyl monomers having cationic amine or quaternary ammonium functionalities conform to the formula:

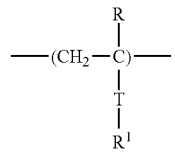

in which T is —O— or preferably —C(O)—, R is H or CH$_3$ and R$^1$ is:

—NH—(CH$_2$)$_n$—N$^+$(R$^2$)(R$^3$)(R$^4$)X$^-$ in which n is an integer from 1 to 8, preferably 1 to 4, each of R$^2$, R$^3$ and R$^4$ are independently hydrogen or a short chain alkyl having from 1 to 4, preferably from 1 to 2 carbon atoms, and X is a counterion. The nitrogen attached to R$^2$, R$^3$ and R$^4$ may be a protonated amine (primary, secondary or tertiary), but is preferably a quaternary ammonium wherein each of R$^2$, R$^3$ and R$^4$ are alkyl groups.

Suitable cationically modified acrylamide polymers have a weight average molecular weight (M$_w$) of at least 500,000 Daltons.

Cationically modified acrylamide polymers that are cationic polymers falling within group (B) preferably have a cationic charge density at pH7 of at least 1.5 meq per gram.

Specific examples of preferred cationically modified acrylamide polymers for use as cationic polymers (B) in the invention are those cationic polymers formed from methacrylamidopropyl trimonium chloride and/or acrylamidopropyl trimonium chloride and copolymers of these monomers with acrylamide, such as polymethyacrylamidopropyl trimonium chloride and acrylamidopyltrimonium chloride/acrylamide copolymer. Suitable materials of this type are commercially available under the trade names POLYCARE 133, from Rhone-Poulenc, and SALCARE SC60, from Ciba Speciality Chemicals, respectively.

Cationically modified polygalactomannans are a preferred class of cationic polymer for use as cationic polymers (B) in the invention.

Polygalactomannans are polysaccharides composed principally of galactose and mannose units and are usually found in the endosperm of certain leguminous seeds such as guar, locust bean, honey locust, flame tree and the like. Guar gum, for example, is composed mostly of a galactomannan with essentially is a straight chain mannan with single membered galactose branches. The ratio of galactose to mannose in the guar polymer is 1:2. Locust bean gum is a polygalactomannan gum of similar molecular structure in which the ratio of galactose to mannose is 1:4.

Preferred cationically modified polygalactomannans for use as cationic polymers (B) in the invention are cationically modified guar gums. Such materials will typically bear cationic substituent groups having the general formula:

—[R—N$^+$(R$^1$)(R$^2$)(R$^3$)]X$^-$, in which R is an alkylene, oxyalkylene, polyoxyalkylene, or hydroxyalkylene group, or combination thereof, R$^1$, R$^2$ and R$^3$ independently represent alkyl, aryl, alkylaryl, arylalkyl, alkoxyalkyl, or alkoxyaryl groups, each group containing up to about 24 carbon atoms, and X is a counterion.

Preferably R is a hydroxyalkylene group of formula —CH$_2$CH(OH)CH$_2$—.

Preferably R$^1$ and R$^2$ are alkyl groups having from 1 to 7 carbon atoms, more preferably from 1 to 3 carbon atoms. Most preferably, R$^1$ and R$^2$ are both methyl.

Preferably R$^3$ is an alkyl group having from 1 to 7 carbon atoms, more preferably from 1 to 3 carbon atoms, most preferably methyl, or an alkyl group having from 8 to 22 carbon atoms, more preferably from 10 to 18 carbon atoms, most preferably dodecyl, or a mixture thereof.

Most preferably, R$^1$, R$^2$ and R$^3$ are all methyl.

Suitable cationically modified guar gums have a weight average molecular weight (M$_w$) of from 10,000 to 10,000,000, preferably from 50,000 to 5,000,000, most preferably from 100,000 to 3,000,000 Daltons.

Preferred cationically modified guar gums have a cationic charge density at pH7 ranging from 0.5 to 2 meq per gram.

Specific examples of preferred cationically modified guar gums for use as cationic polymers (B) in the invention are guar hydroxypropyltrimonium chlorides. Suitable materials of this type are commercially available from Rhodia in their JAGUAR™ series of polymers, such as JAGUAR™ C 13 S and JAGUAR™ C 17.

Mixtures of any of the above described materials may also be suitable.

A preferred mixture comprises a combination of two cationic polymers (B) as defined in general above, in which one of the cationic polymers (B1) has a cationic charge density below 1.2 meq per gram, preferably from 0.5 to 1 meq per gram, and the other of the cationic polymers (B2) has a cationic charge density above 1.2 meq per gram, preferably from 1.2 to 2 meq per gram.

Specific examples of preferred materials for use as cationic polymers (B1) in the invention are guar hydroxypropyltrimonium chlorides having a cationic charge density from 0.5 to 1 meq per gram. A suitable material of this type is commercially available from Rhodia as JAGUAR™ C 13 S.

Specific examples of preferred materials for use as cationic polymers (B2) in the invention are guar hydroxypropyltrimonium chlorides having a cationic charge density from 1.2 to 2 meq per gram. A suitable material of this type is commercially available from Rhodia as JAGUAR™ C 17.

Other preferred materials for use as cationic polymers (B2) in the invention are acrylamidopyltrimonium chloride/acrylamide copolymers having a weight average molecular weight (M$_w$) of at least 500,000 Daltons, and a cationic charge density at pH7 of at least 1.5 meq per gram. A suitable material of this type is commercially available from Ciba Speciality Chemicals as SALCARE SC60.

A most preferred combination of cationic polymers (B1) and (B2) for use in the invention is a combination of guar hydroxypropyltrimonium chloride having a charge density from 0.5 to 1 meq per gram and guar hydroxypropyltrimonium chlorides having a cationic charge density from 1.2 to 2 meq per gram.

The total amount of cationic polymer (B) in compositions of the invention may suitably range from 0.001 to 1.0%, preferably from 0.01 to 0.5%, most preferably from 0.1 to 0.3% by total weight cationic polymer (B) based on the total weight of the composition.

The weight ratio of cationic polymer(s) (A) to cationic polymer(s) (B) in compositions of the invention suitably ranges from 20:1 to 1:20, preferably from 10:1 to 1:10, more preferably from 3:1 to 1:3.

The composition must comprise a cationic polymer other than a cationically modified acrylamide polymer. This means that the composition must comprise more than one class of cationic polymer. The composition may comprise one or more cationic polymers (A) selected from cationically modified acrylamide polymers having a cationic charge density at pH7 of less than 1.0 meq per gram and one or more cationic polymers (B) that is a cationically modified polygalactomannan. Preferred compositions comprise one or more cationic polymers (A) that is a cationically modified cellulose and one or more cationic polymers (B) selected from cationically modified acrylamide polymers having a cationic charge density at pH7 of greater than 1.0 meq per gram, cationically modified polygalactomannans, and mixtures thereof. Particularly preferred compositions comprise one or more cationic polymers (A) that is a cationically modified cellulose and one or more cationic polymers (B) that is a cationically modified polygalactomannans.

Other Ingredients

Compositions according to the invention may contain other ingredients suitable for use in hair cleansing and conditioning compositions. Such ingredients include but are not limited to: fragrance, suspending agents, amino acids and protein derivatives, viscosity modifiers and preservatives.

The invention will now be further illustrated by reference to the following, non-limiting Example.

EXAMPLE

Compositions were prepared having ingredients as shown in Table 1 below.

All ingredients are expressed by weight percent of the total formulation, and as level of active ingredient.

Examples A and B are comparative examples (not according to the invention). Example 1 is a formulation according to the invention.

TABLE 1

| Ingredient | Example A | Example B | Example 1 |
| --- | --- | --- | --- |
| Sodium lauryl sulphate | 13 | 13 | 13 |
| Cocamidopropyl betaine | 1.6 | 1.6 | 1.6 |
| Conditioning agent $^{(1)}$ | 1.2 | 1.2 | 1.2 |
| Cationic polymer $^{(2)}$ | 0.35 | — | 0.1 |
| Cationic polymer $^{(3)}$ | — | 0.35 | 0.25 |
| Pearliser $^{(4)}$ | 1.8 | 1.8 | 1.8 |
| Preservative | qs | qs | qs |
| Perfume | qs | qs | qs |
| Water | To 100 | To 100 | To 100 |

$^{(1)}$ Emulsified silicone with a mean D$_{3,2}$ droplet diameter of less than 0.5 micron.
$^{(2)}$ JAGUAR ™ C 13 S, ex Rhodia
$^{(3)}$ SoftCAT ™ SL 30 Conditioning Polymer, ex Amerchol Corporation
$^{(4)}$ Ethylene glycol distearate Sensory Evaluation Each of the above formulations was scored by 60 trained panellists across a set of performance attributes. The results of the evaluation are shown in Table 2 below:

TABLE 2

| | Attribute | | | |
|---|---|---|---|---|
| | "Tangle/ Matted" after rinse Lower value is best | Wet Squeak after rinse Lower value is best | Wet product Residue (feel) Lower value is best | Dry Finger Through Higher value is best |
| Example A | 4.3 | 5.0 | 4.5 | 6.0 |
| Example B | 4.8 | 5.8 | 3.6 | 5.8 |
| Example 1 | 4.1 | 4.7 | 3.6 | 6.4 |

The test results demonstrate that Example 1 according to the invention gives superior wet and dry conditioning performance to the comparative Examples A and B.

The invention claimed is:

1. An aqueous shampoo composition comprising:
   (i) one or more anionic cleansing surfactants;
   (ii) discrete, dispersed droplets of a water-insoluble conditioning agent with a mean droplet diameter ($D_{3,2}$) of 4 micrometers or less;
   (iii) one or more cationic polymers (A) comprising cationically modified celluloses which are quaternised hydroxyethyl cellulose polymers with cationic substitution of trimethylammonium and dimethyl dodecylammonium; and
   (iv) one or more cationic polymers (B) comprising guar hydroxypropyltrimonium having a charge density of from 0.5 to 2 meq per gram.

2. A composition according to claim 1, wherein (B) is used in a mixture comprising a guar hydroxypropyltrimonium having a charge density of 0.5 to 1 meq and a guar hydroxypropyltrimonium having a charge density of from 1.2 to 2 meq per gram.

3. A composition according to claim 1 in which the anionic cleansing surfactant is selected from the group consisting of sodium lauryl sulphate, sodium lauryl ether sulphate (n) EO, (where n is from 1 to 3), sodium lauryl ether suiphosuccinate (n) EO, (where n is from 1 to 3), ammonium lauryl sulphate, ammonium lauryl ether sulphate(n) EO, (where n is from 1 to 3), sodium cocoyl isethionate and lauryl ether carboxylic acid (n) EO (where n is from 10 to 20), and mixtures thereof.

4. A composition according to claim 1 in which the water-insoluble conditioning agent is emulsified silicone.

5. A composition according to claim 1 in which the discrete, dispersed droplets of water-insoluble conditioning agent have a mean droplet diameter ($D_{3,2}$) of 0.5 micrometer or less.

* * * * *